(12) United States Patent
Dubson

(10) Patent No.: US 10,639,203 B2
(45) Date of Patent: May 5, 2020

(54) PORTABLE ELECTROSPINNING DEVICE

(71) Applicant: NICAST LTD., Lod (IL)

(72) Inventor: Alexander Dubson, Rehovot (IL)

(73) Assignee: NICAST LTD., Lod (IL)

( * ) Notice: Subject to any disclaimer, the term of this patent is extended or adjusted under 35 U.S.C. 154(b) by 157 days.

(21) Appl. No.: 15/592,372

(22) Filed: May 11, 2017

(65) Prior Publication Data

US 2017/0239094 A1 Aug. 24, 2017

Related U.S. Application Data

(63) Continuation-in-part of application No. PCT/IL2015/051086, filed on Nov. 10, 2015.

(60) Provisional application No. 62/077,916, filed on Nov. 11, 2014.

(51) Int. Cl.
*D01D 5/00* (2006.01)
*A61F 13/00* (2006.01)

(52) U.S. Cl.
CPC .. *A61F 13/00017* (2013.01); *A61F 13/00063* (2013.01); *D01D 5/003* (2013.01); *D01D 5/0061* (2013.01); *D01D 5/0084* (2013.01); *D01D 5/0092* (2013.01); *D10B 2509/022* (2013.01)

(58) Field of Classification Search
CPC .................................................. D01D 5/0061
See application file for complete search history.

(56) References Cited

U.S. PATENT DOCUMENTS 6,753,454 B1 6/2004 Smith et al.
7,794,219 B2 9/2010 Dubson et al.

FOREIGN PATENT DOCUMENTS

| CN | 202968788 U | 6/2013 |
|----|-------------|--------|
| CN | 203754859 U | 8/2014 |
| WO | WO/2010/059127 A1 | 5/2010 |
| WO | WO/2014/118585 A2 | 8/2014 |
| WO | WO/2016/075688 A1 | 5/2016 |

OTHER PUBLICATIONS

Shi-Cong Xu et al.,"A battery-operated portable handheld electrospinning apparatus", Nanoscale, Issue 29, 2015.
Mouthuy et al. "Performances of a portable electrospinning apparatus", Biotechnology Letters, Original Research Paper, May 2015, vol. 37, Issue 5, pp. 1107-1116.
International Search Report of PCT/IL2015/051086, dated Feb. 29, 2016.
Written Opinion of the International Search Authority of PCT/IL2015/051086, dated Feb. 29, 2016.

*Primary Examiner* — Ryan M Ochylski

(57) ABSTRACT

A handheld device for producing electrospun fibrous mat comprises: a housing configured to be handheld by a user; a container accommodating at least one electrospinning medium; at least a nozzle in fluid communication with the container; a mechanism dispensing the medium from the container via said nozzle; an auxiliary electrode surrounding the nozzle; and a power supply providing electric potentials to the nozzle and the auxiliary electrode. The housing comprises an electrically conductive portion configured to be gripped by the user during operation. The electrically conductive portion is connected to the power supply.

15 Claims, 8 Drawing Sheets

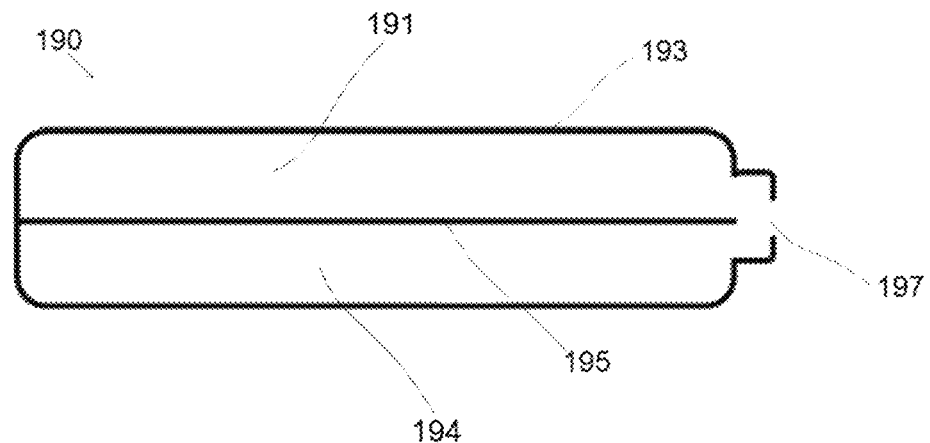
Fig. 6C
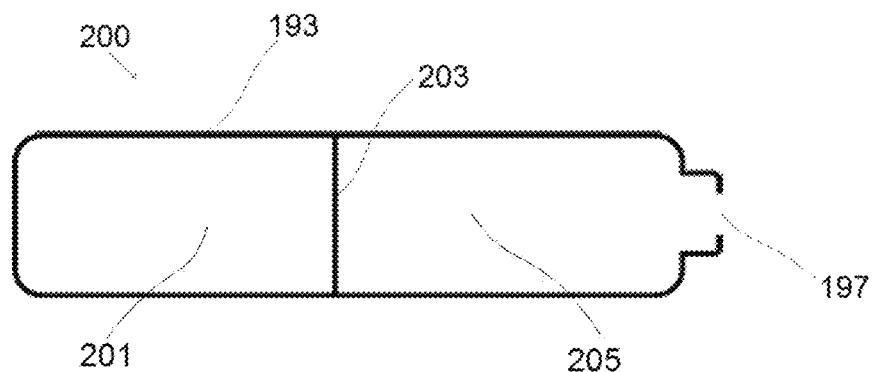
Fig. 6D
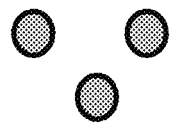 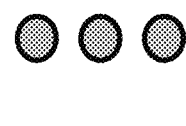  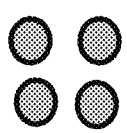
Fig. 7A     Fig. 7B     Fig. 7C     Fig. 7D

PORTABLE ELECTROSPINNING DEVICE

CROSS-REFERENCE TO RELATED APPLICATIONS

This application is a Continuation-in-Part of PCT International Application No. PCT/IL2015/051086, filed Nov. 10, 2015, which claims priority from U.S. Provisional Application No. 62/077,916, filed Nov. 11, 2014.

FIELD OF THE INVENTION

The present invention relates to an electrospinning device and, more particularly, to a portable electrospinning device useful in providing mat-like coatings applicable in different field of technology.

BACKGROUND OF THE INVENTION

Electrospinning is a simple and effective method for producing fibers from tens of nanometers to micrometers. In the electrospinning process, a polymer solution from a reservoir is ejected to a small opening of a capillary by means of Coulomb repulsion of charges that are accumulated at the tip of a pendant droplet as soon as an electrical potential applied between the capillary and a collecting body increases beyond a critical value. As the charged jet travels to the collector, it readily dries out, forming nonwoven fibrous mats depositing on the collector. Due to the ability of fibrous mats and their porous nature, electrospun fibrous webs could be excellent functional wound dressing materials. The porous nature of these mats is highly suitable for the drainage of the wound exudates and, allows appropriate permeation of atmospheric oxygen to the wound. They can be specially made to prevent wounds from attacks of microbes, thus to refrain the wound from possible infections, which would ultimately result in delayed healing.

WO/2010/059127 discloses a portable electrospinning apparatus for generating fibres comprising: at least one reservoir for holding at least one electrospinning medium; an outlet for dispensing the electrospun fibres; a grounded electrode for contacting a surface onto which the fibres are deposited; and a hollow elongate device adapted to connect to the outlet, the hollow elongate device being capable of directing the dispensed fibres towards a pre-determined direction. The present invention also provides a construct for grounding at least one surface, wherein the construct is flexible to substantially conform to the shape of the at least one surface. This is the direct citation from the original document.

U.S. Pat. No. 6,753,454 discloses a novel fiber comprising a substantially homogeneous mixture of a hydrophilic polymer and a polymer which is at least weakly hydrophobic. The fiber optionally contains a pH adjusting compound. A method of making the fiber comprises electrospinning fibers of the substantially homogeneous polymer solution. A method of treating a wound or other area of a patient requiring protection from contamination comprises electrospinning the substantially homogeneous polymer solution to form a dressing. An apparatus for electrospinning a wound dressing is disclosed.

U.S. Pat. No. 7,794,219 discloses an electrospinning device for generating a coat from a liquefied polymer. The device comprises: (a) a dispenser for dispensing the liquefied polymer; (b) a cavity having a longitudinal axis, comprising a first system of electrodes; the dispenser and the first system of electrodes being constructed and design such that the liquefied polymer is dispensed from the dispenser and forms a plurality of polymer fibers moving along the longitudinal axis; and (c) a mechanism for relocating the polymer fibers out of the cavity, in a direction of an object, so as to generate a coat on the object.

Shi-Cong Xu et al (Nanoscale, 2015, 7, 12351) describes an electrospinning apparatus (BOEA) based on miniaturization and integration. The device gets liberated from the conventional heavy power supply, achieves the tight integration of functional parts and can be operated by a single hand due to its small volume (10.5×5×3 cm3) and light weight (about 120 g). Different polymers such as polyvinylpyrrolidone (PVP), polycaprolactone (PCL), polystyrene (PS), poly(lactic acid) (PLA) and poly(vinylidene fluoride) (PVDF) were electrospun into fibers successfully, which confirms the stable performance and good real-time control capability of the apparatus. These results demonstrate that the BOEA could be potentially applied in many fields, especially in biomedical fields such as skin damage, wound healing, rapid hemostasis, etc.

Pierre-Alexis Mouthuy (Biotechnol Lett (2015) 37:1107-1116) reports about a small, battery-operated electrospinning apparatus which enables control over the voltage and the flow rate of the polymer solution via a microcontroller. It can be used to electrospin a range of commonly used polymers including poly(e-caprolactone), poly(p-dioxanone), poly(lactic-co-glycolic acid), poly(3-hydroxybutyrate), poly(ethylene oxide), poly(vinyl acohol) and poly (vinyl butyral). Moreover, electrospun meshes are produced with a quality comparable to a benchtop machine. It is shown that the portable apparatus is able to electrospray beads and microparticles. Finally, we highlight the potential of the device for wound healing applications by demonstrating the possibility of electrospinning onto pig and human skins. Portable electro spinning devices are still at an early stage of development but they could soon become an attractive alternative to benchtop machines, in particular for uses that require mobility and a higher degree of flexibility, such as for wound healing applications.

An electrospinning device for producing a polymer dressing for protecting wound can be very useful in the field environment. The prior art documents disclose electrostatic portable devices operable only in case of grounding a surface of fiber deposition. Effective grounding of a specific patient's skin area is a complicated technical problem. Hence, there is a long-felt and unmet need to provide a handheld device for producing electrospun fiber dressing operable in case of natural grounding of the patient's body. Additionally, the aforesaid handheld device should be enabled to modify features of an obtained coating by means of reconfiguring an applied electrostatic field.

SUMMARY OF THE INVENTION

It is hence one object of the invention to disclose a handheld device for producing electrospun fiber mat. The aforesaid device comprises: (a) a housing configured to be handheld by a user; (b) a container accommodating at least one electrospinning medium; (c) at least one nozzle in fluid communication with said container; (d) a mechanism dispensing said medium from said container via said nozzle; (e) an auxiliary electrode surrounding said nozzle; and a power supply having providing electric potentials to said nozzle and said auxiliary electrode.

It is a core purpose of the invention to provide the housing comprising an electrically conductive portion configured to be gripped by said user during operation; said electrically conductive portion is connected to said power supply.

Another object of the invention is to disclose the auxiliary electrode which is displaceable along said nozzle.

A further object of the invention is to disclose the auxiliary electrode having a shape selected from a group consisting of: a circular barrel; an oval barrel, a sphere, an ellipsoid and any combination thereof.

A further object of the invention is to disclose the dispensing mechanism comprising a piston insertable into said container for outsqueezing said electrospinning medium via said nozzle.

A further object of the invention is to disclose the container which is a carpule, a syringe, a barrel and any combination thereof.

A further object of the invention is to disclose the container and said nozzle integrated into a single element.

A further object of the invention is to disclose at least one of said container and said nozzle which is disposable.

A further object of the invention is to disclose the dispensing mechanism comprising a container bed configured for receiving said container when said electrospinning medium is squeezed from said container by said piston.

A further object of the invention is to disclose the container mechanically deformable such that said electrospinning medium is squeezed out from said container.

A further object of the invention is to disclose the container which is at least partially made of a material pierceable by said nozzle when exerted by said piston to establish a fluid communication between said container and nozzle.

A further object of the invention is to disclose the container comprising at least two sealed compartments successively pierceable by said nozzle to successively feed content of said compartments to said nozzle.

A further object of the invention is to disclose the power supply is of a unipolar type.

A further object of the invention is to disclose the unipolar power supply is configured for providing a potential selected from the group consisting of a positive potential, a negative potential and alternatively positive and negative potentials.

A further object of the invention is to disclose the power supply provided with two spaced apart start buttons such that said device is gripped by both hands of an operator during operation thereof.

A further object of the invention is to disclose the device comprising at least two laser light sources emitting light beam meeting at a predetermined distance for producing an optimal electrospun fiber mat.

A further object of the invention is to disclose the electrically conductive portion electrically connected to a surface to be coated by a conductive wire.

A further object of the invention is to disclose a method of producing electrospun fiber mat. The aforesaid method comprises the steps of: (a) providing a handheld device for producing electrospun fiber mat; said device comprising: (i) a housing configured to be handheld by a user; (ii) a container accommodating at least one electrospinning medium; (iii) at least one nozzle in fluid communication with said container; (iv) a mechanism dispensing said medium from said container via said nozzle; (v) an auxiliary electrode surrounding said nozzle; (vi) a power supply providing an electric potential to said nozzle and said auxiliary electrode; said housing comprises an electrically conductive portion configured to be gripped by said user during operation; said electrically conductive portion is connected to said power supply; (b) gripping said device by an operator/health care provider; (c) directing said device to location to be coated/dressed; (d) applying electric potentials to said nozzle and said auxiliary electrode relative to said conductive portion; (e) electrospinning said medium.

A further object of the invention is to disclose the method comprising a step of displacing said auxiliary electrode along said nozzle to control a dimension and structure of an obtained fiber mat.

A further object of the invention is to disclose the method comprising a step of outsqueezing said electrospinning medium via said nozzle by said dispensing mechanism; said dispensing mechanism comprises a piston insertable into said container.

A further object of the invention is to disclose the method comprising a step of receiving said container into a container bed of said dispensing mechanism when said electrospinning medium is squeezed from said container by said piston.

A further object of the invention is to disclose the method comprising a step of mechanically deforming said container such that said electrospinning medium is outsqueezed from said container.

A further object of the invention is to disclose the method comprising a step of piercing said container at least partially made of a material pierceable by said nozzle when exerted by said piston to establish a fluid communication between said container and nozzle.

A further object of the invention is to disclose the method comprising a step of successive piercing said container comprising at least two sealed compartments to successively feed content of said compartments to said nozzle.

A further object of the invention is to disclose the step of applying electric potentials is performed by a unipolar power supply.

A further object of the invention is to disclose the step of applying electric potentials comprising applying a potential selected from the group consisting of a positive potential, a negative potential and alternatively positive and negative potentials.

A further object of the invention is to disclose the method comprising a step of activating said power supply by two spaced-apart start buttons such that said device is gripped by both hands of an operator during operation thereof.

A further object of the invention is to disclose method comprising a step of positioning said device by means of at least two laser light sources emitting light beam meeting at a predetermined distance for producing an optimal electrospun fiber mat.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which

FIGS. 6A to 6D are schematic diagrams of alternative embodiments of a container accommodating a polymer solution to be electrospun;

FIGS. 7A to 7D are schematic diagrams of alternative embodiments of a nozzle arrangement.

DETAILED DESCRIPTION OF THE INVENTION

Figure 1:
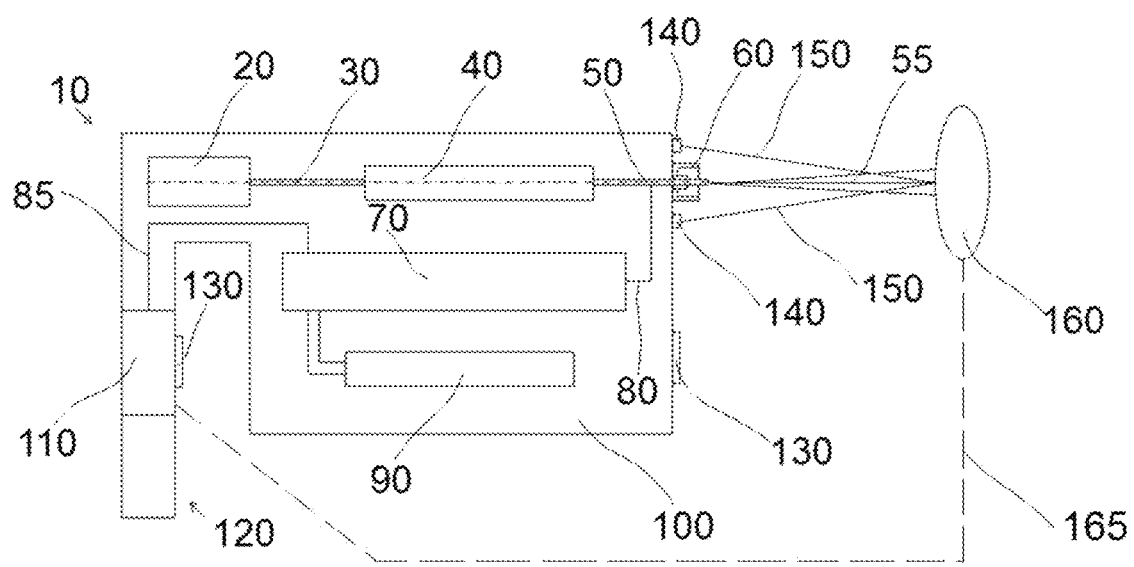
FIG. 1 is a schematic diagram of a handheld device for producing electrospun fiber mat.

The following description is provided, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide a handheld device for producing electrospun fiber mat and a method of using the same.

Electrospinning process is characterized by establishing a closed electric circuit including an air span between a high voltage electrode and a surface to be coated. For purpose of the present invention, it is implied that the surface to be coated is healthy or damaged skin and any kind of wounds having any location on the patient's body. Non-medical applications are also in the scope of the present invention such as coating of art work, fruits etc.

The electrospinning process is operable on condition that an electric current arises within the abovementioned air span. The electric current across the air span includes two main components:
 a. a current originated from transferring charges carried by elemental fibers onto the surface to be coated; the elemental fibers are charged due to induction (contact) charging; charging brought about by collision with air ions within a corona discharge field;
 b. a current of air ions which is relatively low, but can rise with increase in electric field intensity stemming from increase in applied voltage, shortening the air span and ignition/progressing of the corona discharge.

As mentioned above, the electrospinning device is operable if its electric circuit is closed. The closed electric circuit is provided by means of concurrent grounding a high voltage power supply and a surface to be coated.

It should be appreciated that a total value of charge transfer current is in a range between $10^{-7}$ and $10^{-8}$ A and voltage of 30 kV. It follows thence that the resistance of the electric circuit should not exceed $10^{12}$-$10^{11}$ $\Omega$. It is believed that internal resistance of the human body is real and has a value of 500-700$\Omega$. Electric impedance of an external skin layer (epidermis) is characterized by real and capacitive components connected in parallel. Assuming that an area of the electrode located on a handle of a hand-held electrospinning device (the handle is grippable by the user's hand) is several square cm, impedance value of operator-spinning device interconnection can be estimated as $10^{10}$ k$\Omega$.

Thus, grounding resistance (ratio of voltage at the grounded electrospinning device to operational current) is sufficiently low to provide reliable operability for an electrospinning device not including direct electrical connection (by electric wire) to the surface to be covered as known in the art. According to the present invention, the electric circuit is closed via an electrode located on the handle of the electrospinning device and body of the electrospinning device operator.

According to one embodiment of the present invention, the electrospinning device is also connected to a collector body by a conductive cable.

At an end of the needle electrode, polymer solution acquires an electric charge. Then, when a force of electrostatic repulsion is stronger than a surface tension force, particles of the semiliquid substance are originated.

Neoformed polymer fibers are charge carriers and move within the air span from the needle electrode to the surface to be coated under the electrostatic force Fc given by the following expression:

$$Fc=qE,$$

where q is an electric charge and E is electric field intensity.

Also, the gravity, inertial, aerodynamic and electrostatic repulsion forces should be taken into account. In the vicinity of the coated surface, there are forces which can be interpreted as Coulomb forces originated from fictive mirror charges located behind the coated surface.

Practically, electrostatic forces define dimension and configuration of the originated polymer jet pass and, consequently, geometry of the obtained electrospun coating.

Generally, change in distance between the needle electrode and the surface to be coated results in alteration of area of the obtained coating, its thickness and porosity in the case of constant time of electro spinning. For example, polymer fibers flying along a longer distance between the needle electrode and the surface to be coated lose more solvent by means of evaporation, and the resultant coating is characterized by higher density (lower porosity). In other words, area, thickness and porosity of the obtained coating can be modified according to specific needs by means of reconfiguring the applied electrostatic field. Additionally, the coating density depends on kinetic energy of the flying polymer fibers which is a function of applied voltage and the distance between the needle electrode and the surface to be coated.

An arrangement of the handheld electrospinning device having a needle high voltage electrode and a collector/patient's body surface can be described as a needle-plane configuration which is characterized by the conic jet pass and coating profile is similar to the jet pass geometry. In case of constant flow rate of the polymer solution, change in a distance between the needle electrode and the collector/patient's body surface results in change in coating thickness. Thicker coating characterized lower apparent density (higher porosity) corresponds to shorter distance between the needle electrode and collector/patient's body surface. The shorter distance brings about higher rate of thickness growth and higher solvent content within the coating.

Thus, coating thickness can be controlled by means of changing the distance between the needle electrode and collector/patient's body surface. It should be emphasized that a range of available thicknesses is limited by concomitant changes in coating density and fiber diameter.

It should be emphasized that an area of the obtained coating can be controlled also by means of introducing an auxiliary focusing electrode (deflector) into the electrostatic field in proximity of the needle electrode.

Reference is now made to FIG. 1, presenting a schematic diagram of a handheld device for producing electrospun fiber mat 10. An electrical circuit comprises a battery 90, energizing a high voltage power supply 70. One terminal of the high voltage power supply 70 is connected to by a wire 80 to an auxiliary electrode 60. According to one embodiment of the present invention, the electrodes 50 and 60 are at equal electric potentials and the resultant electrostatic field moving the polymer fiber from the needle electrode 50 to a surface to be coated 160 is characterized as a superposition of electric fields generated by the needle and auxiliary electrodes 50 and 60, respectively. Another terminal of the power supply 70 is connected by a wire 85 to a conductive portion 110 of a device handle 120. The conductive portion 110 is configured to be gripped by a hand of an operator (not shown). The impedance value corresponding operator-spinning device interconnection was estimated above. A mechanical arrangement comprises a housing 100 having at least one portion 120 configured to be handheld by a user; a container 40 accommodating at least one electrospinning medium; a nozzle (needle electrode) 50 in fluid communication with the container 40; a motor 20 and a piston 30 driven by the motor 20. The piston 30 exerts the container such that the accommodated electrospinning medium is squeezed out the nozzle (needle electrode) 50.

According to the present invention, an exemplary embodiment of the auxiliary electrode 60 has a toroid shape; thereat the needle electrode 50 is coaxially nested within the toroid auxiliary electrode 60. Any position of the needle electrode 50 relative to the auxiliary electrode 60 including a projecting position and a recessed position and mutual electrode movability are in the scope of the present invention.

The aforesaid needle electrode 50 and auxiliary electrode 60 are made of a conductive material. An electric field configuration created by the electrodes 50 and 60 depends on their relative position (projecting/recessed position) and a circumferential gap between the needle electrode 50 and an inner surface of the auxiliary electrode 60.

A deeper position of the needle electrode 50 within the auxiliary electrode 60 and a small circumferential gap result in reduction in an area of the obtained coating.

According to one embodiment of the present invention, device 10 is provided with two spaced apart start buttons 130. An operator can actuate device 10 only if he/she grips device by both hands. Specifically, one button 130 is located on a handle 120 and another on front surface under auxiliary electrode 60.

It is known in the art that properties of a produced mat depend on a distance between a needle electrode 50 and an object 160 to be dressed (distance between electrodes). Device 10 is provided with two laser light sources 140 which assist in positioning device 10 relative to object 160. Laser beams 150 are arranged such that their point of intersection is at a predetermined distance of forming an optimal mat by flow of charged polymer fibers 55. Thus, positioning device 10 constitutes placing the intersection point onto a surface of object 160.

The portable electrospinning device can include an optical detector (not shown) preprogrammed to assess an obtained area of the mat and its uniformity and instruct a user to optimize the mat. The aforesaid sensor can be a part of a control circuitry preprogrammed to automatically stop the electrospinning process, when the predetermined deployment characteristics are reached.

According to another embodiment, the device of the present invention comprises a distance gauge (not shown) measuring the distance between the auxiliary electrode and the skin. The control circuitry can be preprogrammed to stop deployment (disconnect the electrodes from high voltage power supply) when the distance is below a predetermined distance.

Such safety mechanism prevents improper device operation, operation by unqualified personnel or accidental situations. Distance detection may be achieved by IR distance detector or camera located on the front of the device or any other tool.

According to one embodiment of the present invention, conductive portion 110 of device 10 is connected to a patient by a conductive wire 165 for better focusing the jet on surface 160 to be coated.

Figure 2A:
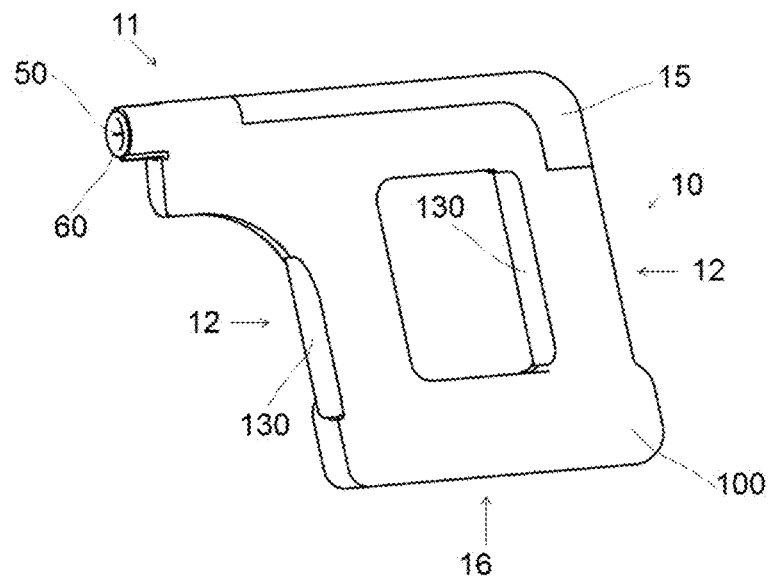
FIGS. 2A and 2B are general and partial perspective views of a handheld device for producing electrospun fiber mat, respectively.
Figure 2B:
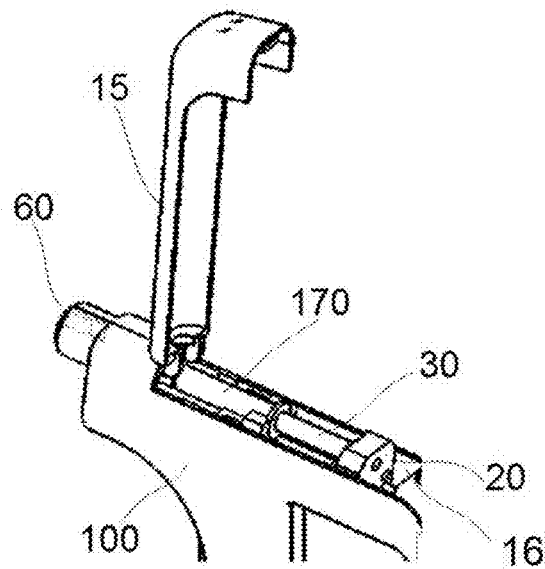

Reference is now made to FIGS. 2A and 2B, presenting general and partial perspective views of a handheld device for producing electrospun fiber mat, respectively. Specifically, FIG. 2A shows device 10 of the present invention characterized by ergonomic friendliness. Here, numerals 130 refer to activation bars which should be concurrently gripped by hands (not shown) of a user during the operation of device 10.

According to the exemplary design, device 10 has nozzle 50 and auxiliary electrode 60 in upper portion 11 of device 10, the portion 12 to be gripped in the middle thereof and high voltage converter (not shown) in bottom part 16. Such configuration provides ergonomic friendliness of device 10 during operation.

FIG. 2B illustrates a specific embodiment comprising syringe-like container 170 accommodating a polymer solution (not shown) to be electrospun. Electric motor 20 propels plunger rod 30 which expels the polymer solution via nozzle. A compartment 16 accommodating element 20, 30 and 170 is closable by cover member 15.

Figure 3:
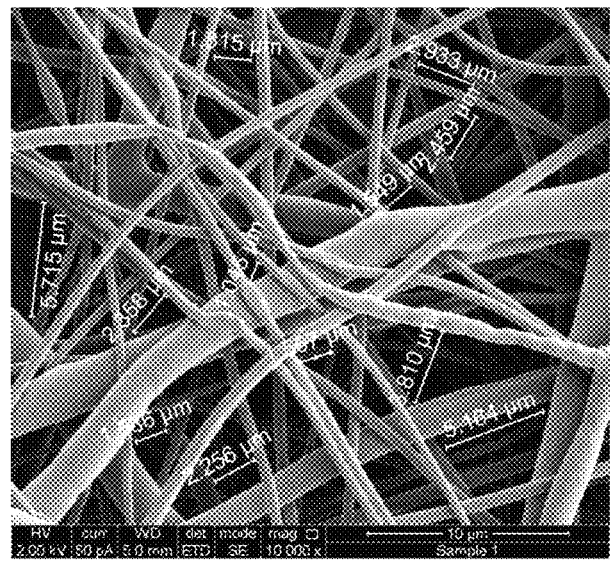
FIG. 3 is a microphotograph of an electrospun coating.

Reference is now made to FIG. 3, presenting a microphotograph of an electrospun fiber mat. The present invention relates to producing electrospun mat with pore size in the range of 1 µm which is small enough to block bacteria entry having the typical size of 0.5-2 µm.

The electrospun mat has the pore size between 0.2 µm and 50 µm. It should be mentioned that the pore size is defined by the largest circular equivalent diameter inside the pore. The effective pore size is practically much smaller due to a multilayered structure of the mat in which the nanofibers are randomly oriented. Although a single pore might be larger than typical bacteria, the obtained structure of the pore network will prevent further bacteria passage.

The antibacterial mat is also effective against fungi penetration (typical size of 1-15 m). In some embodiments the electrospun mat with the pore size smaller than 50 nm can prevent penetration of viruses having the typical size of 20-200 nm.

Figure 4:
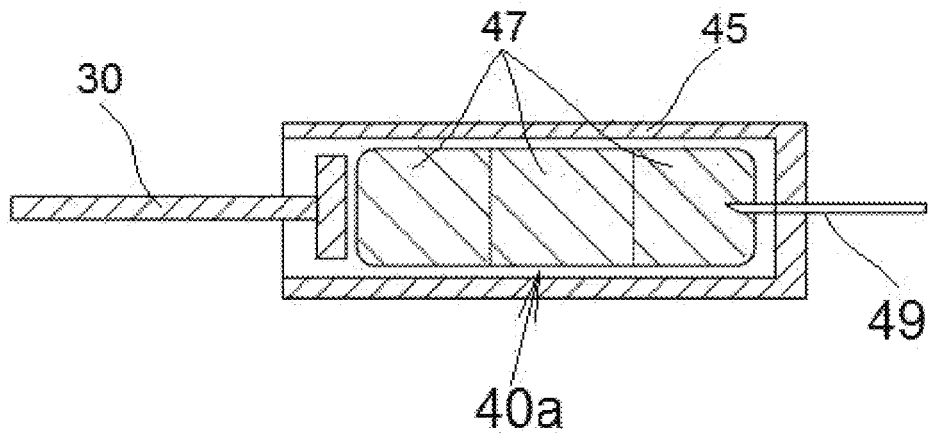
FIG. 4 is a cross-sectional view of a dispensing mechanism with a multi-compartmental container.

Reference is now made to FIG. 4, presenting a dispensing mechanism with an exemplar container 40a comprising three compartments 47. The container is disposed into container bed 45. Needle 49 is protruded into barrel such that, when container 40a is pressed by piston 30 against container bed 45, compartments 47 are successively pierced by nozzle 50 and content of aforesaid compartments is fed to needle electrode 50 via needle 49. Use of compartmented container 40a provides an opportunity of producing multilayer mats without replacement of container 40 during operation of device 10. A device comprising a plurality of nozzles fed by one container is also in the scope of the invention. The device of the present invention can include also a plurality nozzles individually connected to containers accommodating materials to be electro spun.

Figure 5A:
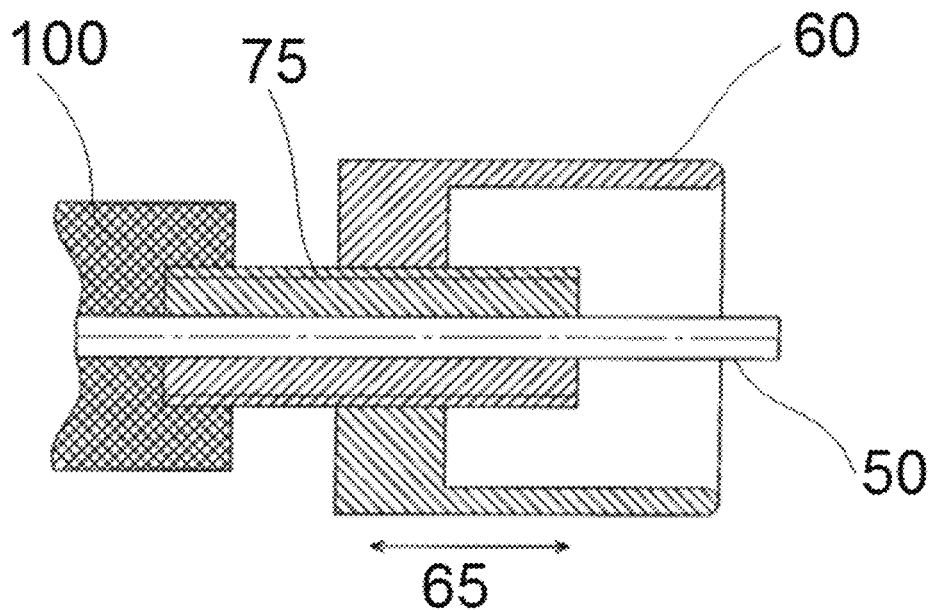
FIG. 5A is a cross-sectional view of an auxiliary electrode.

Reference is now made to FIG. 5A, presenting a cross-sectional view of a needle electrode 50—auxiliary electrode 60 arrangement. A collar member 75 is disposed between the needle electrode 50 and auxiliary electrode 60 and provides mutual coaxial movability of the electrodes 50 and 60.

Figure 5B:
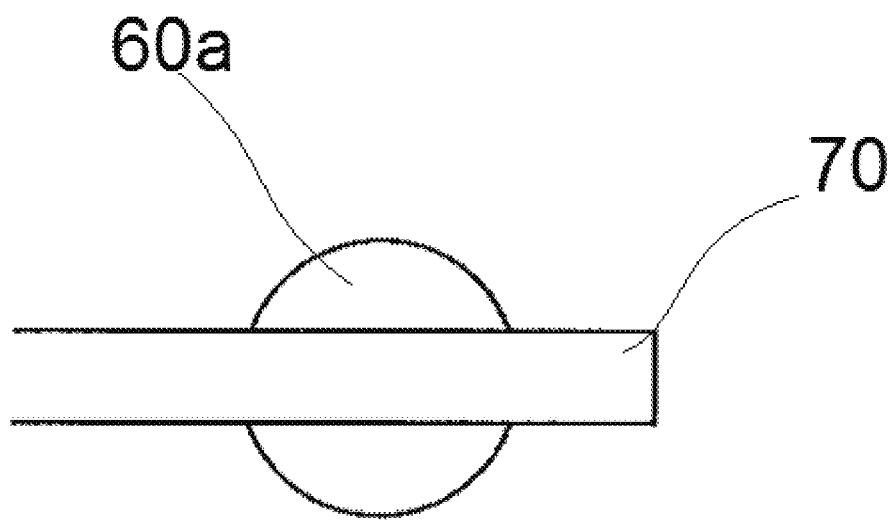
FIGS. 5B to 5D are exemplary embodiments of an auxiliary electrode.
Figure 5C:
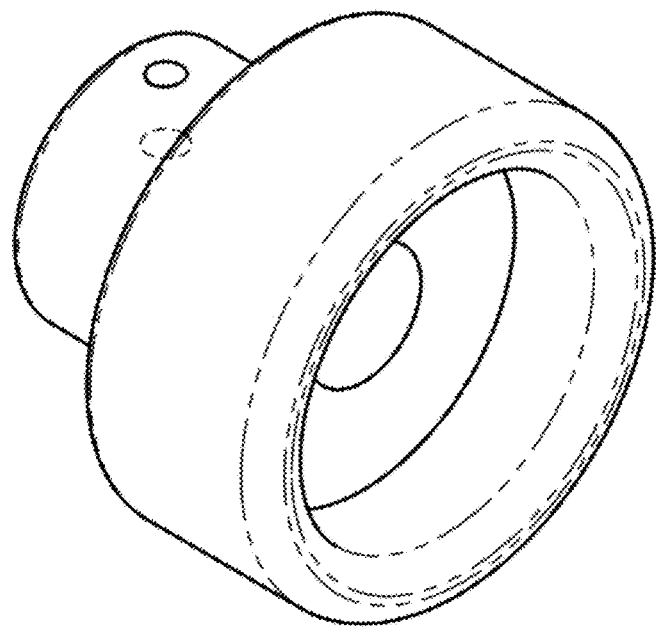
Figure 5D:
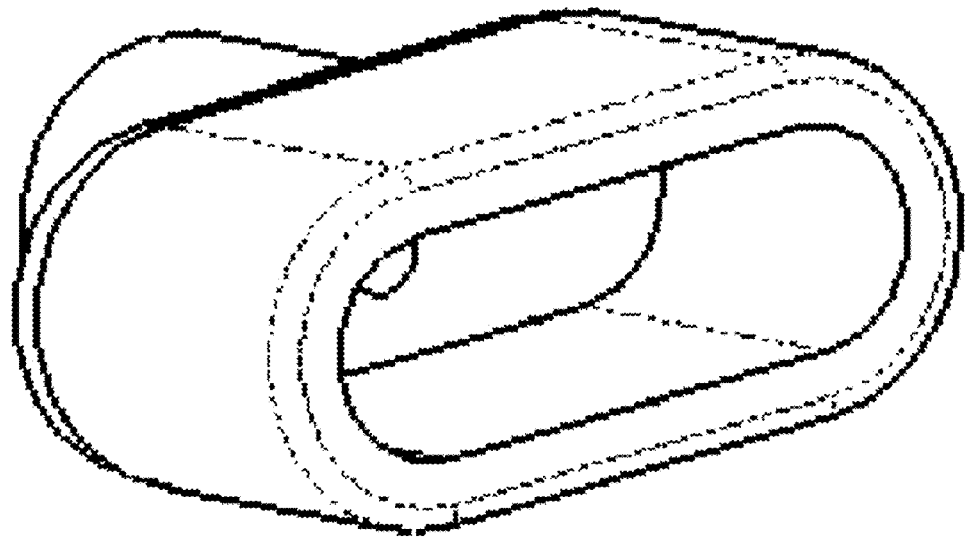

Reference is now made to FIGS. 5B to 5D, presenting alternative embodiments of the auxiliary electrode 60.

Figure 6A:
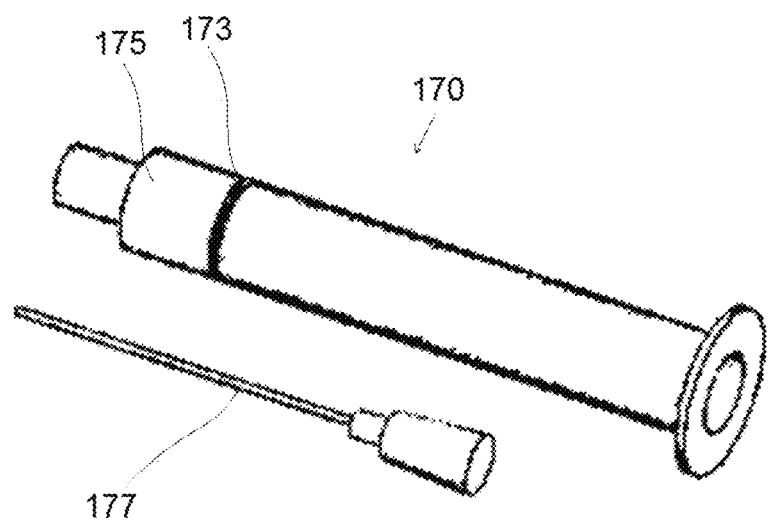
Figure 6B:
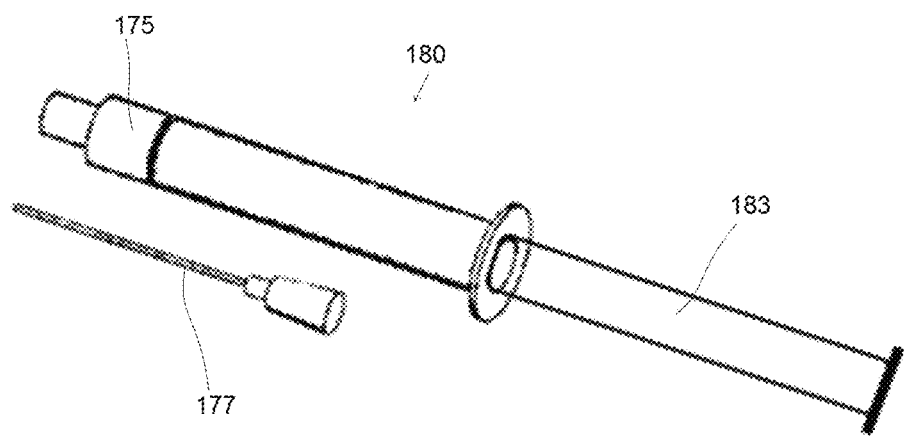

Reference is now made to FIGS. 6A and 6B presenting schematic diagrams of alternative embodiments of a container accommodating a polymeric solution to be electro spun. In FIG. 6A, container 170 comprises internal plunger 173 expelling a content of injection compartment 175 into cannula 177. An alternative embodiment 180 shown in FIG. 6B includes plunger rod 183. An acoustic sensor or a pressure sensor (not shown) indicating depletion of the polymeric solution is also in the scope of the present invention.

Reference is now made to FIGS. 6C and 6D, presenting multi-compartmental container 190 formed by shell 193. Container comprises at least two compartments 191 and 194 divided by partition 195 accommodating at least two electrospinning media. The aforesaid two media are mixable under deformation of said 190 and expellable via outlet port 197. According to an alternative embodiment, multi-compartmental container 200 having at least two compartments 201 and 205 divided by partition 203 can be activated in a predetermined order such that a sandwich mat including a number of layers with required characteristics is formed.

The device enables formation of multi-layered nanofibrous structures by sequential or parallel deposition of nanofibers. Each layer may possess unique chemical, physical and therapeutic properties: controlled water absorption, controlled water vapor transmission rate, specific mechanical properties, release of active ingredients, non-adherence features, etc. The layers can be deposited in a sequential manner, layer by layer or in parallel.

Porosity practically obtainable in the electrospun nanofibrous mats can be varied from large pores useful for facilitating tissue growth to extremely small pores blocking any tissue growth and acting like a polymeric film.

Reference is now made to FIGS. 7A to 7D presenting schematic diagrams nozzle arrangements. In order to speed up the process of producing the polymer mat, the nozzle can be multiplied. The optional geometries are shown in FIGS. 7A to 7D. Each container accommodating an electrospinning solution can be connected to one or several nozzles. The distance between 2 adjacent needles is in the range between 10 mm and 40 mm and more specifically, between 20 and 30 mm.

Polymer fibers originated during electrospinning process are characterized by high electric resistance of $10^{-12}$-$10^{-15}$ $\Omega\cdot$cm. On the one hand, high electric resistance of the polymer fibers enables containment of the fibers on a surface to be coated by means of Coulombian forces. Initially, the surface to be coated can be considered as a grounded surface charged opposite to a charge of the needle/auxiliary electrode. Then, especially in case of a low conductive coating substrate, the polymer fibers deposited on the surface to be coated form a surface charge. In other words, like-charge polymer fibers repel each other by the Coulombian forces.

Coating a surface having a deep profile is also attributed to a complicated technical problem. The patient's body also can be characterized as a combination of bulged and recessed areas. It should be appreciated that motion path of the charged fibers is according to electrostatic lines of force closing on projecting parts. The recessed areas can be interpreted as potential wells where the charged polymer fibers cannot pass through. Thus, the recess areas remain not coated.

More uniform coating can be provided by a pulse mode of the electrospinning process. Specifically, the high voltage power supply applies a train of alternative (negative and positive) potentials to needle/auxiliary electrodes arrangement at frequency ranging between 0.1 and 10 Hz. In this case, the motion path of the charged fibers is defined not only by electrode potentials, but also by interaction between charges carried by the coating which has been already formed and the fibers flying across the air gap between the electrodes arrangement and the coating. The pulse mode conveys polymer fibers to the areas which were inaccessible for the conventional electrospinning technology due to coating surface charge. In the case of the pulse mode, elemental coating layers obtained during single voltage pulses electrically neutralize each other. As result, the coating surface becomes electrically neutral.

Figure 8A:
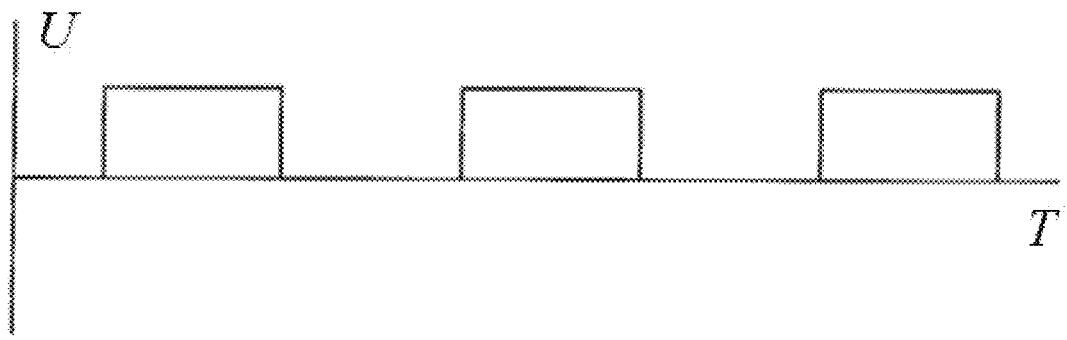
FIGS. 8A to 8C are exemplary graphs of output voltage generated by a unipolar power supply.
Figure 8B:
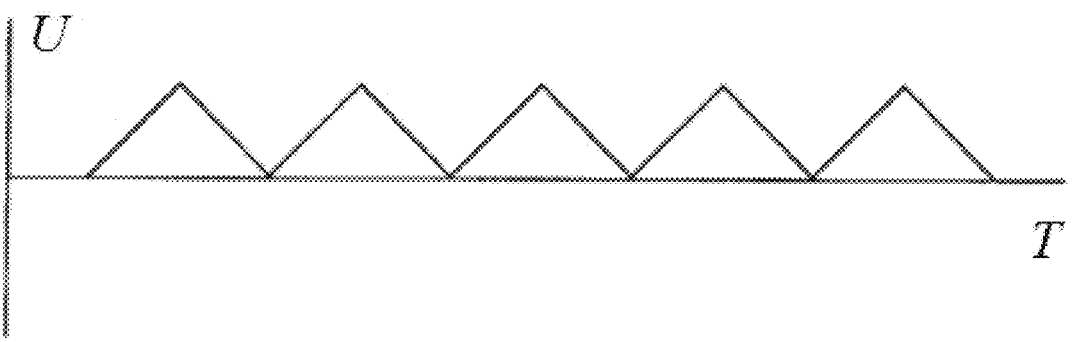

Reference is now made to FIGS. 8A and 8B, presenting graphs of exemplar trains of electric voltage pulses applied to the electrode arrangement.

FIG. 8A shows a preferable form of an output voltage generated by the unipolar power supply. The output voltage is characterized by a train of square voltage pulses. The polymer fibers are accelerated in the electrostatic field and continue flying to the surface to be coated due to kinetic energy which has been gained before in the electrostatic field. Inertial motion of the flying polymer fibers with no electrostatic field can be interpreted as motion of a particle within a potential well, when the particle achieves a well bottom.

An achievable form of the output voltage generated by the unipolar power supply is presented in FIG. 8B. Square voltage pulses are smoothed due to reactive impedance of power supply circuitry.

Figure 8C:
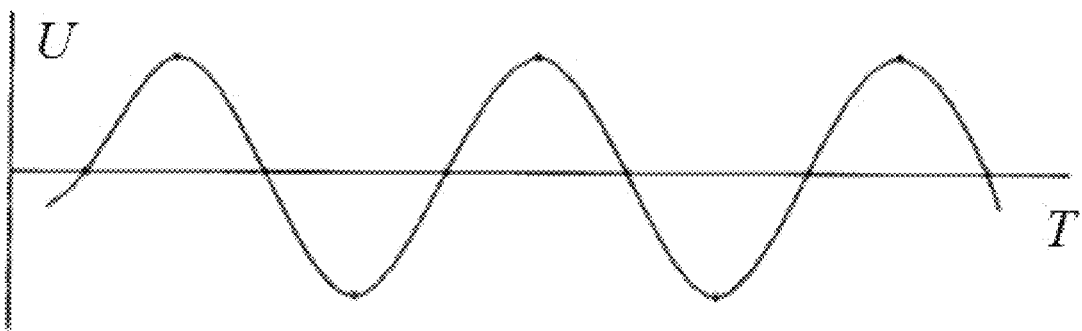

According to one embodiment of the present invention, a coating of increased thickness can be obtained by means of electrospinning process with a form of the output voltage presented in FIG. 8C. The charge which is accumulated on the surface to be coated in case of the continuous unipolar electrospinning process is neutralized by means of alternating polarity of the voltage applied to needle and auxiliary electrodes.

In some embodiments, electrospinning solution can comprise Active Pharmaceutical Ingredients (APIs) or other molecules such as anti-bacterial/anti fungus/anti-inflammatory/anesthetics/analgesics/growth factors/collagens/stem cells substances.

Specifically, a solution of a polymer in water or organic solvents may be admixed with various molecules to provide further therapeutic functions to the electrospun mat, or to improve its biological/chemical/physical features. The mixture will be electrospun in a single operation to create a composite mat composed of polymeric nanofibers incorporating the additive molecules.

Alternatively, the deployment of the APIs can be done separately, for example by deployment of the APIs in separate layer, sometimes, before or after the deployment of the polymer. List of possible additives may include one or more of the following:

Antibacterial substances: Ag (ionic or metallic), PHMB, SSD, Iodine, metal oxides NPs, antibiotics, charcoal. These substances are effective against Gram positive and/or Gram negative bacteria. Various clinical indications are prone to bacteria development; these include burns, wounds and cuts. Incorporation of antibacterial substances into the electrospun mat creates a composite structure with superior properties.

Anti-inflammatory: Ibuprofen, curcumin. Electrospun mat with intrinsic anti-inflammatory properties is useful for clinical applications such as wounds and cuts.

Growth factors—incorporation of growth factors into the electrospun mat to facilitate tissue integration for scaffolding applications.

Anesthetics: Lidocaine—for the treatment of severe pain and discomfort associated with clinical situation.

Analgesics: Ibuprofen

Silicon—control of hydrophilicity/hydrophobicity of the electrospun mat through incorporation of silicon based substances.

Collagen—enabling superior skin rehabilitation.

Honey—various therapeutic effects associated with honey can be combined with the electrospun mat.

Adherence—adding bio glue to the solution.

APIs deployment may include also a combination of 2 or more ingredients simultaneously.

Electrospun wound mats created in situ using the portable electrospinning device of the present invention provide improved adherence to the wound. The nanofibers deployed from the device reach the wound bed (or any other collecting surface) and adhere due to electrostatic (charge transfer from the charged nanofibers to the collector) and chemical interactions. The nanofibers follow the microscopic contour of the wound, because they are equidimensional in comparison with collagen fibers. In other words, a conformal contact between the deployed nanofibers and the wound surface is established at a microscopic level without air gaps. The contact between the electrospun mat and the wound surface can be chemically controlled and tailored for specific applications by means of addition of agents of interest such as hydrophilic additives or pre-treatment of the wound bed.

In some embodiments, different color transparency of the mat can be provided. The mat can turn transparent in contact with the wound due to moisture absorption. A transparent mat facilitates simple and touch-free evaluation of the wound by medical personnel during the healing process following the mat application.

In some embodiments, the device generates an electrospinning mat for direct body surface coating such that the produced electrospun mat follows the body morphology/contour/roughness.

The electrospinning process produces a polymeric solution jet which turns into nanofibers while moving through the electrostatic field between the device and the collector surface. The fibers deposit onto the surface following its microscopic and macroscopic structure, contour, geometry and morphology.

In some embodiments the system enables multi-layer deposition, each layer can have different characteristics.

In some embodiments, the electrospun mats are applicable to the following clinical indication: burn wounds, diabetic wounds, cuts, surgical wounds, chronic wounds, donor site wounds, venous ulcers. The electrospun mats are also applicable in aesthetics and dermatology.

The nanofibrous structure of the electrospun mat because of the similarity to the structure of the extracellular matrix enables effective hemostasis, cell respiration, effective oxygen and water vapor transmission and keeps an adequate moisture level in the area of the wound. The electrospun mat facilitates healing, skin regeneration and quality scarring.

The invention claimed is:

1. A handheld device for producing electrospun fibrous mat; said device comprising:
   a. a housing having at least one portion configured to be handheld by a user;
   b. a container accommodating at least one electrospinning medium;
   c. at least one nozzle in fluid communication with said container;
   d. a mechanism dispensing said medium from said container via said nozzle;
   e. an auxiliary electrode surrounding said nozzle;
   f. a power supply providing difference of electric potentials on said nozzle and said auxiliary electrode;
   wherein said housing comprises an electrically conductive portion configured to be gripped by said user during operation.

2. The device according to claim 1, wherein at least one of the following is true:
   a. said auxiliary electrode is displaceable along said nozzle;
   b. said auxiliary electrode has a shape selected from a group consisting of: a circular barrel; an oval barrel, a sphere, an ellipsoid and any combination thereof;
   c. said dispensing mechanism comprises a piston exerting said container for squeezing out said electrospinning medium via said nozzle;
   d. said container is selected from the group consisting of a carpule, a syringe, a barrel and any combination thereof,
   e. said container and said nozzle are integrated into a single element;
   f. at least one of said container and said nozzle is disposable,
   g. said dispensing mechanism comprises a container bed configured for receiving said container when said electrospinning medium is squeezed from said container by said piston.

3. The device according to claim 1, wherein said container is at least partially made of a material pierceable by said nozzle when exerted by said piston to establish a fluid communication between said container and nozzle.

4. The device according to claim 3, wherein said container comprises at least two sealed compartments pierceable by said nozzle to feed content of said compartments to said nozzle.

5. The device according to claim 1, wherein at least one of the following is true:
   a. said container comprises at least two compartments accommodating at least two electrospinning media; said at least two media are mixable under deformation of said container;
   b. said container comprises at least two sealed compartments successively pierceable by said nozzle to feed content of said compartments to said nozzle in a successive manner;
   c. said container comprises at least two sealed compartments pierceable by at least two independent nozzles in parallel to feed content of said compartments in the same manner.

6. The device according to claim 1, wherein at least one of the following is true:
   a. said power supply is of a unipolar type;
   b. said power supply is provided with two spaced apart start buttons such that said device is gripped by both hands of an operator during operation thereof;
   c. said device comprises means for positioning said device relative to a location of an electrospun fiber mat to be made;
   d. said device comprises safety means deactivating said device when a distance between said nozzle and said surface to be coated is shorter than a predetermined value;
   e. said electrically conductive portion is electrically connected to a surface to be coated by a conductive wire,
   f. said electrically conductive portion is electrically connected to a neutral terminal of said power supply.

7. The device according to claim 1, wherein said unipolar power supply is configured for providing a potential selected from the group consisting of a positive potential, a negative potential and alternatively positive and negative potentials.

8. The device according to claim 1, wherein said positioning means comprises at least two laser light sources emitting light beam for marking a predetermined distance for producing an electrospun fiber mat.

9. The device according to claim 1, wherein said container comprises a barrel and a piston pressing out said at least one electrospinning medium into said nozzle.

10. The device according to claim 1, wherein said electric potential difference ranges between 5 kV to 50 kV.

11. The device according to claim 10, wherein said electric potential difference is between 20 kV to 30 kV.

12. The device according to claim 1, wherein said fibrous mat comprises at least two layers made of different electrospinning media.

13. The device according to claim 1, wherein a flow rate per said nozzle ranges between 1 ml/hour to 20 ml/hour.

14. The device according to claim 13, wherein a flow rate per said nozzle ranges between 5 ml/hour to 10 ml/hour.

15. The device according to claim 1, wherein said electrospinning medium comprises at least one pharmaceutical agent.

* * * * *